(12) United States Patent
Marshall

(10) Patent No.: US 6,479,278 B2
(45) Date of Patent: Nov. 12, 2002

(54) **DETECTION OF *HELICOBACTER PYLORI* IN THE STOMACH**

(76) Inventor: Barry Marshall, 40 Beatrice Road, Dalkeith 6009 (AU)

( * ) Notice: Subject to any disclaimer, the term of this patent is extended or adjusted under 35 U.S.C. 154(b) by 0 days.

(21) Appl. No.: 09/824,870

(22) Filed: Apr. 3, 2001

(65) Prior Publication Data

US 2001/0012623 A1 Aug. 9, 2001

Related U.S. Application Data

(63) Continuation-in-part of application No. 08/832,332, filed on Mar. 26, 1997, now Pat. No. 6,228,605, which is a continuation of application No. 08/489,816, filed on Jun. 13, 1995, now abandoned.

(51) Int. Cl.$^7$ ................................................. C12M 1/34
(52) U.S. Cl. ....................................... 435/287.9; 435/34
(58) Field of Search .......................... 435/287.9, 286.1, 435/287.3, 287.4, 287.7, 34

(56) References Cited

U.S. PATENT DOCUMENTS

| | | |
|---|---|---|
| 3,121,041 A | 2/1964 | Stern et al. |
| 3,383,283 A | 5/1968 | Brindamour |
| 6,228,605 B1 * | 5/2001 | Marshall ...................... 435/34 |

* cited by examiner

Primary Examiner—Ralph Gitomer
(74) Attorney, Agent, or Firm—Sheldon H. Parker

(57) ABSTRACT

A method for the in vivo detection of urease-producing helicobacter in the upper stomach is disclosed. The dense carrier is divided into two separate groups which are combined with separate reagent indicators, one of which also contains urea. The carriers are food soluble products, preferably sugar beads having a diameter of approximately 0.2 to 3.0 mm. The treated carriers and urea are encapsulated in a soluble capsule which is administered to a patient. The density of the carriers cause the capsule to migrate to the gastric mucosa, where the capsule, but not the reagents, is dissolved, placing the reagents and urea in direct contact with the gastric mucosa. The urea reacts with any urease present in the stomach by creating ammonia, which increases the pH in the immediate vicinity of the urea containing carrier and indicator beads. The two reagents react differently, through color change, to the increase in pH, which is viewed through use of an endoscope. A preferred first reagent is bromothymol blue (dibromothymolsulfonphthalein), which changes yellow in the presence of urease, and a preferred second reagent is phenol red (phenolsulfonphthalein), which turns red in the presence of urease.

7 Claims, 1 Drawing Sheet

DETECTION OF *HELICOBACTER PYLORI* IN THE STOMACH

Cross-Reference to Related Patent Application

This application is a continuation in part of patent application Ser. No. 08/832,332 filed on Mar. 26, 1997, now U.S. Pat. No. 6,228,605 which is a continuation of Ser. No. 08/489,816 filed on Jun. 13, 1995, now abandoned the disclosures of which are incorporated herein by reference as though recited in full.

BACKGROUND OF THE INVENTION

1 Brief Description of the Invention

The instant invention relates to a novel method of in vivo diagnosis of upper gastrointestinal diseases.

2 Brief Description of the Prior Art

Factors adversely affecting the function of the gastrointestinal system in humans are exceedingly varied in their nature. Such disorders may arise in the upper or lower gastrointestinal tracts, or both. There is a broad range of causes of gastrointestinal disorders, including genetic, physiological, environmental and psychogenic factors. Accordingly, the diagnosis and management of these disorders can be exceptionally difficult.

Among the chronic disorders of the upper gastrointestinal tract are those which fall under the general categories of gastritis and peptic ulcer disease. The upper gastrointestinal tract is generally defined as including the esophagus, the stomach, the duodenum, the jejunum and ileum. Peptic ulcers are lesions of the gastrointestinal tract lining, characterized by loss of tissue due to the action of digestive acids and pepsin. It has generally been held that peptic ulcers are caused by gastric hypersecretion, decreased resistance of the gastric lining to digestive acids and pepsin, or both. Gastritis is, by definition, an inflammation of the stomach mucosa. In practice, though, the disorder is manifested by a broad range of poorly-defined, and heretofore inadequately treated, symptoms such as indigestion, "heart burn", dyspepsia, and excessive eructation.

As with the management of any disorder, the rapid, precise, and accurate diagnosis of gastrointestinal disorders is of paramount importance. The typical means used to diagnose the gastrointestinal disorder presented by a given patient will depend upon such factors as the nature and severity of symptoms, the overall health of the individual, the medical history of the patient, the need for a specific diagnosis in order to implement a treatment with reasonable likelihood of success, and the availability of diagnostic devices. However, the diagnostic methods typically employed in the art are often slow, cumbersome, costly, and may yield equivocal or inaccurate results. Thus, for patients not having severe symptoms, a precise diagnosis of a gastrointestinal disorder might not be attempted. Such patients may simply be treated with conventional therapies, such as with antacids or drugs which inhibit stomach acid secretion. While such therapies might provide temporary symptomatic relief, a cure is often not effected. More effective treatments may depend upon better diagnoses of the actual underlying gastrointestinal disorder. In particular, it has been discovered that many such gastrointestinal disorders are mediated by infection of gastric mucosa by *Helicobacter pylori*. *H. pylori* is a Gram-negative spiral organism which produces the enzyme urease. The organism is predominantly found beneath the mucus layer of the luminal aspect of the gastric epithelium and in the gastric pits. Helicobacter can be diagnosed by blood test for antibodies, breath test, or biopsy of the stomach lining. Antibodies, however, can remain positive for many months after the bacteria have been eradicated. The presence of antibodies presents a falsely positive result in approximately 10 to 15% of patients. Biopsies are relatively quick; however, they add time, expense and risk. Although relatively minor, there is a 1 in 20,000 risk of bleeding from a biopsy site. Biopsies cannot be performed on patients who have a tendency to bleed, such as patients with hemophilia and liver disease. Additionally, it has recently been found that helicobacter is patchy, thereby requiring multiple biopsies to obtain 100% accuracy. The cost for a biopsy is approximately $100. Biopsies also increase the risk of the person handling the tissue being exposed to HIV. If a urease test is used, the biopsy sample must be placed in the test by the nurse, thereby requiring an additional person during the test.

The prior art has disclosed testing for gastrointestinal disorders, the majority of which have been in vitro. Many tests have also been disclosed using urea and indicators.

Marshall, 4,748,113 discloses compositions and methods for the diagnosis of gastrointestinal disorders involving urease. Methods include obtaining a gastric sample material and contacting the material with a composition including urease and an indicator.

Marshall 4,830,010, discloses methods for the diagnosis of gastrointestinal disorders. The method steps include administration of urea-containing compositions prior to assay.

Steward et al, 5,139,934 disclose substrate compositions and method of urease assay. The method is an in vitro immunoassay that includes the use of pH indicators.

Nagatsu et al, 4,147,692 disclose methods and compositions for measuring enzymatic activities and correlating such activities with various disease states.

Kraffczyk et al, 3,873,369 disclose colorimetric indicators for the determination of urea.

Vasquez et al, 4,851,209 disclose in vivo diagnostic procedures for the clinical evaluation of gastrointestinal ulcer disease using radioactive isotopes. Procedures involve prior administration of a diagnostic pharmaceutical followed by scintigraphic imaging of the gastrointestinal area of interest with scintigraphic imaging equipment.

Although the use of urease or other indicators has been used in combination with pH indicators, all except Vasquez et al are conducted in vitro.

The instant invention discloses a method of detecting the alkaline pH change in vivo. The test dramatically cuts down the number of biopsies required and is safe for patients having any bleeding tendencies while being rapid and low cost. Additionally, through the color change, it can be determined if the change is a true positive or a false positive reaction.

BRIEF DESCRIPTION OF THE DRAWINGS

The advantages of the instant disclosure will become more apparent when read with the specification and the drawings, wherein.

SUMMARY OF THE INVENTION

Figure 1:
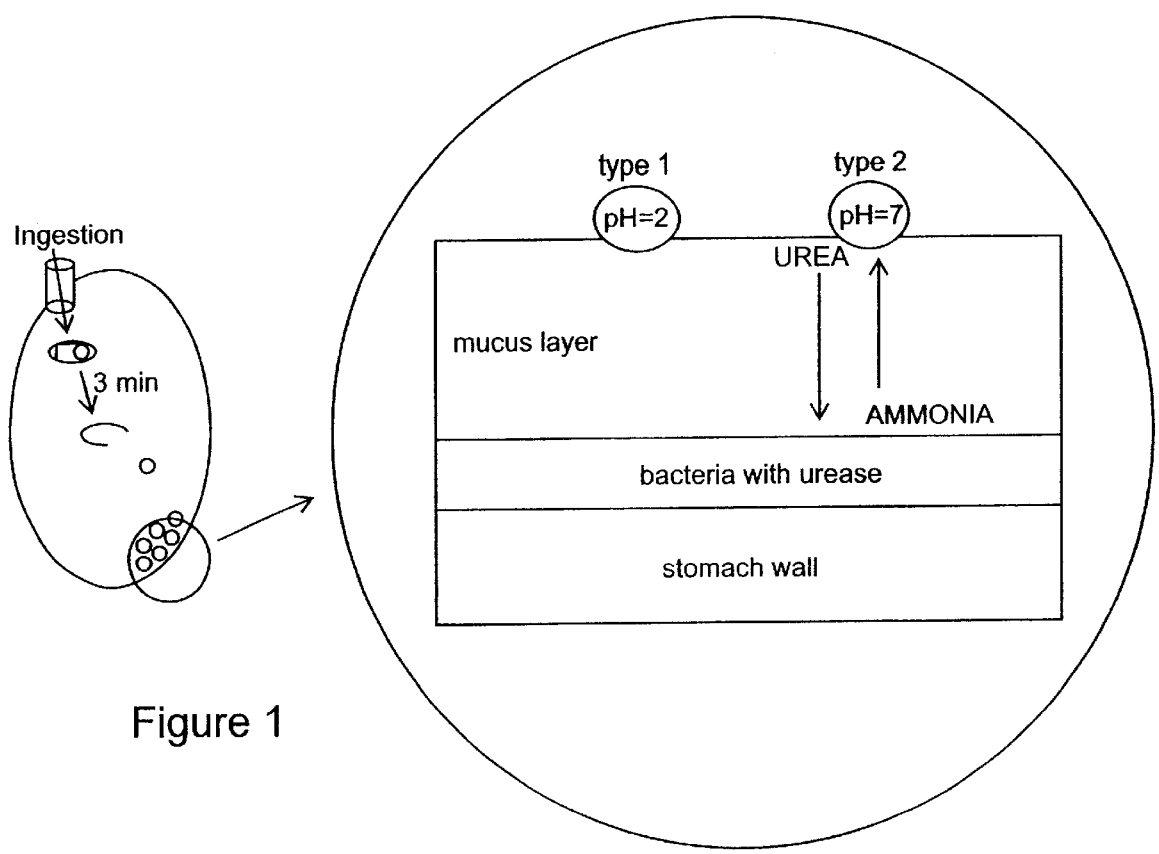
FIG. 1 illustrates the location of the beads in the stomach and the urea/ammonia transfer.

A method and diagnostic device for the in vivo detection of urease-producing helicobacter in the upper stomach is disclosed. A dense pharmaceutically acceptable carrier is used which is divided into two separate groups, the first combined with a first reagent indicator and the second combined with a second reagent indicator and urea. The carriers are preferably food soluble products, such as sugar beads having a diameter of approximately 0.2 to 3.0 mm. The carrier and reagents can be combined through coating the carrier or mixing the carrier and reagent. The treated carriers and urea are encapsulated in a pharmaceutically acceptable soluble capsule that is then administered to a patient. If desired, a buffer can be added to obtain more specific results. The density of the carriers cause the capsule to migrate to the gastric mucosa where the gastric juices dissolve the reagents and urea containing capsule, thereby placing the two reagents and urea combination in direct contact with the gastric mucosa. The urea reacts with any urease present on the mucosa thereby creating ammonia which causes the pH within the stomach to increase. The two reagents react differently, through color change or other indices, to the increase in pH, which is viewed through use of an endoscope. A preferred first reagent is bromothymol blue (dibromothymolsulfonphthalein), which changes to yellow in the presence of urease, and a preferred second reagent is phenol red (phenolsulfonphthalein), which turns red in the presence of urease.

DETAILED DESCRIPTION OF THE INVENTION

The instant disclosure uses indicators, such as color change, to detect alkaline pH change in the stomach. A change in the colors of the indicators, as viewed during endoscopy, identifies a pH change within the stomach. Depending upon the combination of indicator changes, the presence, or lack of presence, of helicobacter, or *H. pylori,* organisms is indicated.

Urea has the formula $H_2NCONH_2$ and is a naturally occurring product of protein metabolism. Gastric materials from humans or other animals having gastrointestinal disorders contain relatively large quantities of urease (urea aminohydrolase) which hydrolizes urea to ammonium carbonate or ammonia and carbon dioxide. Normally urease is present in the body in only trace amounts, performing the function of decomposing urea. *H. pylori,* however, increases the amount of urease above normal in the affected areas. The increased urease reacts with the urea administered with the disclosed diagnostic device by creating ammonia, which in turn increases alkalinity, thereby causing an indicator change in response to the alteration of pH.

The color indicators useful in this invention are weak acids with sharply different colors in their dissociated (ionized) and un-dissociated (neutral) states. The indicators useful herein have pKa values of from about 6.5 to about 8.5, preferably from about 7.0 to about 8.0. The color exhibited by the indicator in the present composition will depend upon the pH of the composition, the particular indicator used, and the dissociation constant (Ka) for that indicator (i.e., pKa [log10Ka]. As the color exhibited by the indicator changes over a range of pH values ($pH = log^{10}[H^+]$), the indicators useful in the present compositions change color over a pH range of from about 5.5 to about 9.0, preferably from about 6.5 to about 8.5. The pH of the present compositions are accordingly adjusted to a pH at least about one pH unit lower than the pKa of the indicator used (i.e. having a hydrogen ion concentration [H+] ten times less than (10% of) the hydrogen ion concentration in a solution having a pH equal to the pKa of the indicator). Preferably, the pH is adjusted to a pH about two pH units below the pKa of the indicator.

Adjustment of the pH of the present compositions can be effected by addition of a base (e.g. sodium hydroxide) or an acid (e.g. hydrochloric acid or citric acid). Thus, preferably, the pH of the composition of this invention is adjusted to a pH of from about 5.0 to about 6.5, with the preferred embodiment being from about 5.0 to about 6.0.

The preferred reagents are bromothymol blue (dibromothymolsulfonphthalein) indicator, Reagent 1, and phenol red (phenolsulfonphthalein) indicator, Reagent 2. Other indicators useful herein include p-nitrophenol, neutral red (2-methyl-3-amino-6-dimethylaminophenazine), quinoline blue (cyanine), cresol red (o-cresolsulfonphthalein), and thymol blue (thymolsulfonphthalein). Indicators among those useful herein are described in the The Merk Index (9th ed. 1976), incorporated by reference herein. Reagent 2 has urea added to react with the urease enzyme, if present. The urea penetrates the mucus layer of the stomach to come into contact with the urease-containing bacteria, H. pylori, on the stomach wall. The urea/urease combination creates ammonia which migrates outward through the mucus layer to come into contact with the Reagents.

The urea is added to a soluble, dense carrier at approximately 1–20 grams per kilogram of carrier. The preferred carrier is beads, such as nu-pareil beads, although any dense carrier can be used which has sufficient density to carry the capsule to the stomach mucosa. In the preferred embodiment the Reagents 1 and 2 are put into the stomach in a solid phase, such as beads, which can be individually identified in the stomach. The reagents should be coated onto small diameter beads, preferably 0.2–3.0 mm, with the preferred size being approximately 2 mm. The 2 mm. size of the beads provides the advantages of visibility as well as preventing obstruction of the endoscope in the event not all of the beads dissolve. A suitable method of making such beads would be to use sugar beads, such as nu-pareil seeds, with a mesh size of 25–35. The nu-pareil beads provide the density required to migrate to the mucosa, either in the capsule or after the capsule dissolves. A less dense vehicle, which floats within the gastric juices, would prevent the Reagents from being placed onto the mucosa. U.S. Pat. No. 3,121,041, issued to Stem et al, discloses the use of a plug, impregnated with a radioactive material, in combination with a soluble capsule. The spongy plug disclosed in Stem would float within the gastric juices, providing several disadvantages. In order to obtain the contrasting results of the two reagents, two impregnated sponges must be used within the capsule, thereby increasing manufacturing expenses. The Stem et al patent discloses tapping the sponges into the capsule. The use of two sponges would possibly double the time required to produce the Stem capsule. Additionally, as the sponges would float within the gastric juices, the Reagents would be diluted and possibly affected by the contents of the gastric juices. The Reagents must be placed directly onto the mucosa to allow the urea to migrate to the stomach wall, react with the urease created by the H. pylori, create ammonia, and subsequently alter the pH. To allow for a dilution factor would require increasing the amount of urea used in the capsule. By placing the urea directly onto the mucosa, dilution is reduced to a minimum and therefore a small quantity produces superior accuracy. The beads cannot be coated as commonly known in the time release capsule art, as the reagents on all the beads must be activated simultaneously to obtain a reliable reading. U.S. Pat. No. 3,383,283 to Brindamour discloses time release beads coated with a fatty acid. The fatty acid coating, along with many other coatings, would cause all or some of the beads to float within the gastric juices, again preventing contact with the mucosa.

The disclosed testing procedure is performed in vivo, thereby frequently eliminating the need for a biopsy. In order to view the reagent color change, the beads must remain in a single area. To accomplish this, the beads must not float, but rather lie directly on the mucosa, at the source of the bacteria. It has recently been discovered that H. pylori within the stomach is not continuous or in large areas, but rather patchy within the stomach wall. In the instant disclosure, the natural dispersal of the beads onto the mucosa cover a sufficient area to react with at least one area of *H. pylori* bacteria. Any floating indicators which come in contact with the mucosa on either a temporary or scattered basis, have a narrow chance to come in direct contact with the affected area. Beads which do not dissolve after a few minutes in the stomach can cause an obstruction of the endoscope if they are below the preferred size. Other types of dense vehicles can be used as long as they are capable of absorbing the required reagents and of dissolving within a few minutes. When using a powdered carrier, the reagents are mixed with the carrier, the carrier is allowed to dry, and, if necessary, reground to powder form. The beads have the advantage that coating the beads with the reagents is a simpler, more economical method of obtaining optimum results.

An example of manufacture of the beads would be:
Reagent 1- bromothymol blue indicator
buffer (pH=6.0)
sugarbeads
Reagent 2- phenol red indicator
buffer (pH=6.0)
sugarbeads
urea The beads are preferably encapsulated into a quick-dissolving gelatin capsule for delivery to the stomach in mass and undiluted. The capsule can be swallowed with a small amount of liquid, such as water, to more rapidly deliver the capsule and speed the dissolving of the capsule. If necessary, a buffer, such as citrate, having a pH between 4.0 and 6.0 can be added to the liquid to render the gastric pH initially slightly acid. Reagents applied in liquid form will mix with each other, even if taken separately, providing an indefinite result.

Additional ingredients can be added with the reagents to produce any specific desired results. An example of this would be to buffer an Acid pH with a stable buffer such as citrate buffer at pH 6.0, 30 mls. The buffer can be added to the seed-coating along with the reagents or can be placed in powdered form in the capsule. The use of a buffer adds stability to the shelf life of the capsules.

In FIG. 1 the stomach wall, bacteria with urease, and mucus layers are shown with the reagent beads resting on the mucus layer. As the urea released from the Reagent 2 comes in contact with the urease, ammonia is generated. The ammonia rises through the mucus layer and comes into contact with the Reagent indicators, causing an increase in the pH and the Reagents to change color.

To administer the test, the subject takes one to two capsules with 30 mls. of pH 6.0 buffer immediately before endoscopy. It takes approximately 5 minutes for the endoscope to reach the stomach, at which time the capsules have dissolved and the granules are resting and slowly dissolving on the surface of the gastric mucosa. Through the endoscope, the examining person can detect the color changes of the reagents, if any, which indicate the presence of the helicobacter organisms.

In the following example Reagent 2 is yellow at acid pH, changing to red at alkaline pH and Reagent 1 is yellow at acid pH, changing to blue at alkaline pH. The instant invention relies on a differential color change to identify a true positive from a false positive reaction. It is the differential which is of importance, not the colors themselves and any colors and/or reagents specifically used herein are examples and in no way limit the scope of the invention.

Reading Example I

Negative result, (no urease, stomach is acid)

| Regent 1 (yellow) | | Both remain yellow |
|---|---|---|
| | no urease | |
| Reagent 2 (yellow) | | no pH change occurs |

Reading Example II

False positive result (stomach has an alkaline pH; for example, bile is in stomach or patient salivates excessively)

| Reagent 1 (yellow) | | Changes to blue |
|---|---|---|
| | no urease, pH > 6.5 | |
| Reagent 2 (yellow) | | Changes to red |

Reading Example III

True positive result (stomach is acid but contains urease)

| Reagent 1 (yellow) | urease | Remains yellow |
|---|---|---|
| pH < 6 | | no pH change occurs. |
| Reagent 2 (yellow) | urease | Changes red |
| | | pH rises > 6.5 |

The presence of red and yellow reagent, but not blue reagent, indicates that urease is in the stomach (i.e. Helicobacter).

What is claimed is:

1. A diagnostic device for detection of urease producing *Helicobacter pylori* within a subject's stomach comprising:
   a soluble container, said container containing a combination of:
   (1) a pharmaceutically acceptable first pH indicator with a pH range from about 5.5 to about 9.0, said first pH indicator having a first indicium to indicate an alkaline pH and a second indicium to indicate an acidic pH,
   (2) a pharmaceutically acceptable second pH indicator wcombination, said second pH indicator combination including a second pH indicator with a pH range of from about 5.5 to about 9.0 and having a first indicium to indicate an acidic pH and a third indicium to indicate an alkaline pH range, and a reagent, said reagent reacting with urease to generate ammonia,
      said first pH indicator first indicium and said second pH indicator combination first indicium having the same indicium, and said first pH indicator second indicium and said second pH indicator combination third indicium having different indicium from one another and from said first pH indicator first indicium and said second pH indicator first indicium,
   said first pH indicator and said second pH indicator combination reacting to a presence or absence of urease producing Helicobacter by change, or lack of change, of indicium, wherein:
   both said first pH indicator and said second pH indicator combination indicating an acidic pH indicates an absence of said Helicobacter and said stomach is acidic and there is an absence of urease producing Helicobacter;

said first pH indicator second indicium and said second pH indicator combination third indicium indicating an alkaline pH range indicates said stomach is alkaline and no determination regarding a gastrointestinal disorder can be made; and said first pH indicator first indicium indicating an acidic pH and said second pH indicator combination third indicium indicating an alkaline pH indicates the presence of ammonia and the presence of urease producing Helicobacter.

2. The diagnostic device of claim 1, further comprising:

a first dense carrier, said first dense carrier being pharmaceutically acceptable, soluble in gastric fluids, and having a density sufficient to cause said first carrier to descend through stomach fluids to said stomach's gastric mucosa;

a second dense carrier material, said second dense carrier being pharmaceutically acceptable, soluble in gastric fluids, and having a density sufficient to cause said second carrier to descend through stomach fluids to said stomach's gastric mucosa;

said first dense carrier being combined with said first pH indicator, and said second dense carrier being combined with said second pH indicator combination.

3. The diagnostic device of claim 1, wherein said indicium is color, said first pH indicator first indicium being a first color at an acidic pH and said second indicium being a second color at an alkaline pH and said second pH indicator combination first indicium being said first color at an acidic pH and said second indicium being a third color at an alkaline pH, each of said first pH indicator first indicium and said second pH indicator combination first indicium can be the same color and said first pH indicator second pH indicium and said second indicator combination third indicium being different colors from one another and from said first pH indicator first indicium and said second pH indicator combination first indicium.

4. The diagnostic device of claim 1, wherein said container is a soluble capsule, said soluble capsule containing said first carrier and said second carrier combination and being soluble in gastric fluids.

5. The diagnostic device of claim 2, wherein said first dense carrier material and said second dense carrier material are pharmaceutically acceptable products which sorb said indicators and dissolve in said gastric fluids in about five minutes after reaching said stomach's gastric mucosa.

6. The diagnostic device of claim 2, wherein said first dense carrier material and said second dense carrier material are in the form of beads, thereby facilitating dispersal of said indicators over the mucosa.

7. The diagnostic device of claim 1 wherein said reagent is urea.

* * * * *